US008834338B2

(12) United States Patent
Srivastava et al.

(10) Patent No.: US 8,834,338 B2
(45) Date of Patent: Sep. 16, 2014

(54) DOSIMETRY IMPLANT FOR TREATING RESTENOSIS AND HYPERPLASIA

(75) Inventors: Suresh Srivastava, Setauket, NY (US); Gilbert R. Gonzales, New York, NY (US); Roger W. Howell, Millington, NJ (US); Wesley E. Bolch, Gainesville, FL (US); Radoslav Adzic, East Setauket, NY (US)

(73) Assignee: SnIP Holdings, Inc., The Woodlands, TX (US)

( * ) Notice: Subject to any disclaimer, the term of this patent is extended or adjusted under 35 U.S.C. 154(b) by 1232 days.

(21) Appl. No.: 11/758,937

(22) Filed: Jun. 6, 2007

(65) Prior Publication Data
US 2010/0137673 A1    Jun. 3, 2010

Related U.S. Application Data

(63) Continuation-in-part of application No. 11/351,435, filed on Feb. 9, 2006, now abandoned.

(60) Provisional application No. 60/652,129, filed on Feb. 10, 2005.

(51) Int. Cl.
*A61N 5/00* (2006.01)
*A61F 2/91* (2013.01)
*A61N 5/10* (2006.01)

(52) U.S. Cl.
CPC ....... *A61N 5/1002* (2013.01); *A61N 2005/1019* (2013.01); *A61N 2005/1005* (2013.01); *A61N 5/1014* (2013.01); *A61F 2210/0095* (2013.01); *A61N 2005/1003* (2013.01); *A61F 2/91* (2013.01)
USPC .............................. 600/3; 623/1.15; 623/1.46

(58) Field of Classification Search
USPC ........... 600/1–8; 623/1.1–1.54; 128/897–898
See application file for complete search history.

(56) References Cited

U.S. PATENT DOCUMENTS

| | | | | |
|---|---|---|---|---|
| 5,059,166 | A | 10/1991 | Fischell et al. | 600/3 |
| 5,302,168 | A | 4/1994 | Hess | 600/3 |
| 5,411,466 | A | 5/1995 | Hess | 600/3 |
| 5,484,384 | A | 1/1996 | Fearnot | 600/3 |
| 5,730,698 | A | 3/1998 | Fischell et al. | 600/3 |
| 5,840,009 | A * | 11/1998 | Fischell et al. | 600/3 |
| 5,879,282 | A | 3/1999 | Fischell et al. | 600/3 |
| 6,077,413 | A | 6/2000 | Hafeli et al. | 205/170 |
| 6,099,455 | A * | 8/2000 | Columbo et al. | 600/3 |
| 6,179,789 | B1 * | 1/2001 | Tu et al. | 600/585 |
| 6,187,037 | B1 | 2/2001 | Satz | 623/1.34 |
| 6,322,490 | B1 | 11/2001 | Stack et al. | 600/3 |

(Continued)

OTHER PUBLICATIONS

Supplementary European Search Report and Search Opinion, application No. EP 08826538.4, Jun. 24, 2010.

(Continued)

*Primary Examiner* — Charles A Marmor, II
*Assistant Examiner* — Carrie R Dorna
(74) *Attorney, Agent, or Firm* — Wood Herron & Evans LLP (57) ABSTRACT

The present invention discloses a method of selectively providing radiation dosimetry to a subject in need of such treatment. The radiation is applied by an implant comprising a body member and $^{117m}$Sn electroplated at selected locations of the body member, emitting conversion electrons absorbed immediately adjacent selected locations while not affecting surrounding tissue outside of the immediately adjacent area.

17 Claims, 6 Drawing Sheets

(56) References Cited

U.S. PATENT DOCUMENTS

| | | | |
|---|---|---|---|
| 6,379,380 B1 | 4/2002 | Satz | 623/1.15 |
| 6,383,217 B1 | 5/2002 | Satz | 623/1.34 |
| 6,447,439 B1* | 9/2002 | Vallana et al. | 600/3 |
| 6,503,477 B1 | 1/2003 | Srivastava et al. | 424/1.65 |
| 6,638,205 B1 | 10/2003 | Chan et al. | 600/3 |
| 7,022,136 B2 | 4/2006 | Lundqvist | 623/1.42 |
| 7,045,116 B2 | 5/2006 | Simon et al. | 424/9.1 |
| 7,198,675 B2* | 4/2007 | Fox et al. | 118/500 |
| 2002/0183581 A1 | 12/2002 | Yoe et al. | 600/3 |
| 2003/0036699 A1 | 2/2003 | Strauss | 600/436 |
| 2003/0134142 A1 | 7/2003 | Ivey et al. | 428/646 |
| 2003/0204125 A1* | 10/2003 | Brauckman et al. | 600/3 |
| 2003/0233141 A1 | 12/2003 | Israel | 623/1.15 |
| 2004/0184989 A1 | 9/2004 | Thakur | 424/1.11 |
| 2005/0051437 A1 | 3/2005 | Kurashina et al. | 205/143 |
| 2005/0060021 A1 | 3/2005 | O'Brien et al. | 623/1.15 |
| 2005/0288869 A1 | 12/2005 | Kroll et al. | 702/19 |
| 2006/0235504 A1 | 10/2006 | Gonzales | 623/1.15 |
| 2007/0068823 A1 | 3/2007 | Takizawa et al. | 205/300 |
| 2007/0071676 A1 | 3/2007 | Gonzales et al. | 424/1.49 |

OTHER PUBLICATIONS

International Search Report and the Written Opinion of the International Searching Authority, application No. PCT/US2008/065223, dated Jan. 2, 2009.

Office Action, U.S. Appl. No. 11/351,435, dated Oct. 17, 2007.

* cited by examiner

Figure 3D

DOSIMETRY IMPLANT FOR TREATING RESTENOSIS AND HYPERPLASIA

CROSS-REFERENCE TO RELATED APPLICATIONS

This is a continuation-in-part of U.S. application Ser. No. 11/351,435, filed Feb. 9, 2006, now abandoned which claims the benefit of U.S. Application No. 60/652,129, filed Feb. 10, 2005, the entire content of each of which is hereby incorporated by reference thereto.

STATEMENT OF GOVERNMENT INTEREST

This invention was made with Government support under contract number DE-AC02-98CH10886, awarded by the U.S. Department of Energy. The Government has certain rights in the invention.

FIELD OF THE INVENTION

The present invention relates generally to medical devices such as implants and methods of use of such devices in treatments of certain medical conditions. More particularly, the invention relates to luminal prostheses, such as vascular stents and grafts, which have been prepared to deliver controlled dosages of radiation to treat restenosis and hyperplasia.

BACKGROUND OF THE INVENTION

A number of percutaneous intravascular procedures have been developed for treating stenotic atherosclerotic regions of a patient's vasculature to restore adequate blood flow. The most successful of these treatments is percutaneous transluminal angioplasty (PTA). In PTA, a catheter, having an expandable distal end usually in the form of an inflatable balloon, is positioned in the blood vessel at the stenotic site. The expandable end is expanded to dilate the vessel to restore adequate blood flow beyond the diseased region. Other procedures for opening stenotic regions include directional atherectomy, rotational atherectomy, laser angioplasty, stenting, and the like. While these procedures have gained wide acceptance (either alone or in combination, particularly PTA in combination with stenting), they exhibit certain significant disadvantages.

A particularly common disadvantage with PTA and other known procedures for opening stenotic regions is the frequent occurrence of restenosis, which refers to the re-narrowing of an artery after an initially successful angioplasty. In the absence of stenting, restenosis afflicts approximately up to 50% of all angioplasty patients and is the result of injury to the blood vessel wall during the lumen opening angioplasty procedure. In some patients, the injury initiates a repair response that is characterized by smooth muscle cell proliferation referred to as "hyperplasia" in the region traumatized by the angioplasty. This proliferation of smooth muscle cells re-narrows the lumen that was opened by the angioplasty within a few weeks to a few months, thereby necessitating a repeat PTA or other procedure to alleviate the restenosis.

A number of strategies have been proposed to treat hyperplasia and reduce restenosis. Previously proposed strategies include prolonged balloon inflation during angioplasty, treatment of the blood vessel with a heated balloon, treatment of the blood vessel with radiation following angioplasty, stenting of the region, and other procedures. While these proposed strategies have enjoyed varying levels of success, none has been proven to be entirely successful in substantially or completely avoiding all occurrences of restenosis and hyperplasia.

As an alternative or adjunctive to the above mentioned therapies, the administration of therapeutic agents following PTA for the inhibition of restenosis has also been proposed. Therapeutic treatments usually entail pushing or releasing a drug through a catheter or from a stent. While holding great promise, the delivery of therapeutic agents for the inhibition of restenosis has not been entirely successful.

Of particular interest to the present invention, the use of radiation and "radioactive" stents for inhibiting vascular hyperplasia has been proposed. Radioactive intraluminal endovascular stents prevent neointimal hyperplasia by non-selectively killing dividing cells. The long term consequences of radiation and other stent-delivered therapies on normal heart and on non-cardiac tissue are unknown. Beta particle emitting radioisotopes attached to stents, such as phosphorus-32, deliver 95% of the radiation dose within 4 mm of the stent edge and the radiation dose decreases to less than $\frac{1}{1000}$ of the original dose at five months post implantation. However, the depth or distance (4 mm) into tissue by beta emitters is excessively deep because the majority, if not all the abnormal changes occur in diseased coronary arteries and specifically vulnerable plaque are within a depth of less than 0.33 mm.

For these reasons, it would be advantageous to provide improved medical devices to accurately deliver radiation only to desired areas in order to more effectively and safely treat hyperplasia in the vasculature following angioplasty and other interventional treatments. It would be further desirable if the improved methods and devices were useful for treating other luminal hyperplasia and neoplasia, including tumors and other neoplastic disease which can occlude and otherwise interfere with the functuality of body lumens. A radioactive stent that is used therapeutically to prevent restenosis and that has the additional benefit of being able to be imaged using a gamma camera would be of clinical utility in determining the position of the stent, to determine radioactive dosimetry and decay and potentially to reveal an internal imaging of soft plaque and hard plaque material. The present invention now provides such improved devices and treatment methods that meets the needs in the art.

SUMMARY OF THE INVENTION

The invention relates to an implant comprising a body member and a conversion electron emitting source (CEES) associated with selected locations of the body member, with the CEES providing conversion electrons that are emitted to provide radiation dosimetry immediately adjacent the selected locations while not affecting surrounding tissue outside of the immediately adjacent area. The body member of the implant is configured and dimensioned to conform to organs or fluid vessels associated therewith the selected locations providing CEES in the form of an adherent selective coating at least where the body member contacts the organs or fluid vessels. The body member of the implant includes an expandable scaffold structure so that it can assume a first placement configuration and a second treatment configuration wherein the conversion electrons are emitted by a distance of only between 0.2 and 0.3 mm in tissue.

The invention is also related to a method of selectively providing radiation dosimetry to a subject in need of such treatment. The radiation is applied by placing a CEES adjacent, upon or within an organ or fluid vessel associated with the organ and in a manner such that the selected locations of the organ or vessel receive conversion electrons from the CEES for such treatment. Preferably, this method comprises providing a CEES source that provides hyperplasia inhibiting radiation for treatment of hyperplasia in the subject, wherein the CEES is selectively provided upon an implant which is placed in contact with the organ or fluid vessel to provide the conversion electrons in a selected location for such treatment.

A preferred aspect of this method is to use a stent as the implant, with the stent being is placed within a blood vessel of the subject, and wherein the stent contains the CEES only on selected portions thereof. In this way, the method can provide selective treatment of the organ or fluid vessel by providing a non-uniform concentration of the CEES and at a quantity such that the CEES provides between 1 and 80 mCi 117 mSn with higher amounts provided in locations where greater treatment of adjacent tissue is desired.

Another method according to the invention is for selectively providing radiation dosimetry to a subject in need of same by placing one of the implants disclosed herein adjacent, upon or within an organ or fluid vessel associated with the organ and in a manner such that the selected locations of the implant containing the CEES are provided at least where the body member contacts the organ or fluid vessel to provide conversion electrons thereto from the CEES for such treatment.

In this method, selective treatment of the organ or fluid vessel is achieved by providing the body member with end portions and providing the CEES at a higher concentration at least one end portion of the body member. In one embodiment, each end portion of the body member is provided with a higher concentration of CEES than the remainder of the body member. Alternatively, each end of the body member can be provided with a lower concentration of CEES than in the remainder of the body member. The particular design of the non-uniform application of CEES to the implant can be selected by the skilled artisan depending upon the desired treatment and provision of conversion electrons to tissue.

By these methods, conversion electrons are emitted to selected locations immediately adjacent the CEES or implant while not affecting surrounding tissue outside of the immediately adjacent area for enhanced, selective treatment of the subject.

BRIEF DESCRIPTION OF THE DRAWING FIGURES

The invention is more fully appreciated upon a review of the following detailed description and appended drawing figures which together illustrate and disclose particularly preferred embodiments of the invention, wherein.

DETAILED DESCRIPTION OF THE PREFERRED EMBODIMENTS

The present invention provides improved methods and devices for treating body organs or lumens with controlled dosimetry radiation for a variety of purposes. In particular, organs as well as blood vessels or other body lumens may be treated by implanting a device that includes a CEES to deliver controlled dosages and amounts of radiation to a specific locations. In particular, such a device in the form of a selectively coated stent can be introduced into a blood vessel to deliver such radiation for inhibiting hyperplasia or neoplasia which might otherwise occur therein. In the case of arteries, the conversion electron radiation will also reduce the resulting restenosis which often occurs after angioplasty and other intravascular interventions. As used herein, the term "inhibit" means to reduce hyperplasia by at least 30% relative to the hyperplasia which would occur in the absence of the radiation ("uncontrolled hyperplasia"), typically preventing at least 50% of such hyperplasia, and often preventing 75% or more of the uncontrolled hyperplasia.

The devices of the invention will be exemplified by luminal implants, but the skilled artisan having this disclosure before him or her will certainly be able to configure and design devices for numerous other treatments. For example, the technique and calculations for dosimetry can be used for all conversion electron emitting isotopes. Moreover, the dosimetry calculations are useful for devices besides coronary stents, such as hollow lumen prostate and ureteral stents as well as biliary and other gastro-intestinal stents. The dosimetry can be used to treat cancer as well as atherosclerotic disease and immune and other inflammatory diseases.

Luminal implants are generally known in the art and are preferred devices according to the invention. Such implants are suitable for implantation at a susceptible site to hyperplasia or neoplasia in the vasculature or other body lumen. Such susceptible sites are typically luminal sites which have been injured, or which may become injured, as a result of disease or trauma. Most typically, the injuries may occur following an interventional procedure such as an intravascular intervention that occurs during the treatment of stenotic, thrombotic, or other conditions in a coronary artery or other blood vessel. The most common interventional procedure is balloon angioplasty where a balloon is inflated within the blood vessel in order to widen the lumen. Other vascular interventions include directional atherectomy, rotational atherectomy, laser angioplasty, stenting, and the like. In addition to blood vessels, the methods and devices of the present invention may be used in particular to treat other body lumens, such as ureters, urethras, hepatic ducts, and other body lumens and ducts which are susceptible to impaiiinent by neoplastic disease.

The luminal implants of the present invention will usually comprise an expandable scaffold which can be delivered to the blood vessel or other body lumen in a collapsed configuration and, expanded in situ at a target site by expansion within the body lumen. Such expandable scaffolds will usually be in the form of a "stent" or "graft". Such stents and grafts are well-known and amply described in the patent and medical literature. Typically, the stents and grafts may be either "balloon expandable" where they are formed from a malleable material which is expanded in situ by expansion of a balloon within a lumen of the stent or graft. Alternatively, the stent or graft may be "self expanding", typically being formed from a shape-memory alloy of highly elastic material which allows the stent or graft to be constrained during delivery and released from constraint at the target site within the body lumen. In both cases, the stent or graft will normally provide sufficient radially outward or "hoop" strength in order to help hold the blood vessel or other body lumen open in order to maintain patency of the lumen. Such stents and grafts will typically be delivered to blood vessels immediately following angioplasty or other primary interventional treatments.

Conversion electron emission is a unique form of radiation with low toxicity and specific physico-chemical properties. The conversion electron is an electron ejected from the atom in the process of internal conversion. Internal conversion is a photophysical process producing an isoenergetic radiationless transition between two electronic states of the same multiplicity. When the transition results in a vibrationally excited molecular entity in the lower electronic state, the entity usually undergoes deactivation to its lowest vibrational level, provided the final stage is not unstable to dissociation. A preferred material that exhibits this phenomenon is $^{117m}$Sn, a material that is well disclosed in the scientific literature as being able to deliver conversional electrons at a short range and monoenergetic radiation that, in higher concentrations, has significant anti-neoplastic properties. According to the present invention, in small doses, the conversion electrons from $^{117m}$Sn will produce an anti-inflammatory cellular response to inhibit excess accumulation of cells around and inside an implant, such as a vascular stent. In particular, use of the conversion electron emitting implants is believed to allow for a thin layer of endothelial cell growth on the stent to provide a smooth inner covering to incorporate the device into the artery itself. Such endothelization can help prevent subsequent thrombosis and restenosis of the artery or other blood vessel.

While effective to inhibit hyperplasia and restenosis, the conversion electrons emitted by $^{117m}$Sn, with its low-energy conversion electron emission and short range in tissue, will not produce significant radiation damage to non-hyperplastic and neoproliferative cells. Such limited energy delivery prevents the excessive cell growth at either end of a stent which is been observed with the use of prior radiation-emitting stents, commonly referred to as the "candy wrapper" effect. To reduce the candy wrapper effect, it is necessary to provide different concentrations of CEES along the length of the prosthesis so that there is relatively less or in some cases more radioactivity towards the two terminal ends of the stent in comparison to the radioactivity of the rest of the stent. This differential distribution of radioactivity could also preclude radioactivity exposure to the outer edge of the stent so that only the inner-most (i.e., non-outer edge) of the vessel lumen in contact to the stent is exposed to radioactivity. Alternatively, a higher differential distribution of $^{117m}$Sn radio activity at the stent ends would produce a higher exposure to the artery beyond the scaffolding effect of the stent and to include areas of the vessel or lumen that may have inflammatory activity but which does not require scaffolding.

Methods according to the present invention for inhibiting hyperplasia in body lumens generally comprise implanting a source of conversion electrons in the body lumen. The body lumens will typically be at risk of hyperplasia, including blood vessels, ureters, urethras, arteriovenous dialysis shunts, microvascular arteries, arterioles, veins and venules (especially macular and meningorachidian vessels), vaginal canal, cervical or, esophagus, trachea, bronchioles, bronchi, gastrointestinal tract, ostomies, binary and pancreatic ducts, and the like. The methods of the present invention will find their greatest use, however, in treating arteries for hyperplasia following angioplasty and other primary interventions.

In the present invention, the primary CEES, $^{117m}$Sn, is electroplated onto a scaffold or other suitable luminal prosthesis as described above and adapted to provide a therapeutically effective radiation emission, typically in the range from 0.0125 mCi/mm to 150 mCi/mm, preferably from 0.05 mCi/mm to 10 mCi/mm, most preferably in the range from 0.125 mCi/mm to 0.75 mCi/mm. Implantation typically comprises expanding the scaffold within the body lumen, and specific CEES materials may be any of those described above. $^{117m}$Sn will usually be in metallic form and can be prepared in an accelerator, such as a cyclotron, by transmutation of antimony into no-carrier-added $^{117m}$Sn by high energy proton induced nuclear reactions. The metallic $^{117m}$Sn can be combined with or coupled to the scaffold of a luminal implant in a variety of ways. For example, the $^{117m}$Sn alloy maybe formed directly as a structural component of the scaffold or as the entire scaffold. Alternatively, the $^{117m}$Sn may be electroplated over a portion of a scaffold composed of a different material.

The $^{117m}$Sn may be applied to the entire scaffold, but it is preferred to selectively apply this material only upon certain portions of the scaffold in areas or locations that will deliver the conversion electrons to most efficiently treat the problem or condition. A convenient way to selectively apply this material is by electroplating. A more complete detail of this electroplating method can be found in U.S. patent application Ser. No. 11/758,914, filed Jun. 6, 2007, now U.S. Pat. No. 8,114, 264, issued Feb. 14, 2012, entitled METHOD OF ELECTROPLATING A CONVERSION ELECTRON EMITTING SOURCE IN IMPLANT, the entire content of which is expressly incorporated herein by reference thereto.

In one embodiment of the present invention, $^{117m}$Sn is electroplated onto the ACS MultiLink™ stents. Prior to electroplating, the stents are first thoroughly rinsed to remove adventitious grease and dust particles and a pair of tweezers is inserted into the stent to restrict the $^{117m}$Sn activity to the outside surfaces of the wire.

Then the stents are submerged in the activation and plating solution containing $CoCl_2$ or $NiCl_2$, which generates a "seed" layer to provide better bonding of Sn to steel, and HCl which activates stents by dissolving the passive film on stainless steel. Cobalt or nickel deposition is followed by a quick rinsing with water and transferring to a Sn plating solution which comprises $Sn^{2+}$, $H_2SO_4$, HCl and resorcinol (or gelatin). The electroplating is carried out at room temperature and in the presence of Tl, which reduces the rate of $H_2$ evolution to ensure the quality of Sn coating.

The quality of the Sn coating is checked by standard tests for bonding and adhesion using scotch tape and bending the wire constituting the stent at 90 degrees. If the deposit does not peel off with the tape, or no cracks occur upon bending, the adhesion can be considered satisfactory.

The scaffold may comprise any conventional stent or graft material, typically being a metal. As noted above, the metal may actually be formed in part or entirely of tin, including $^{117m}$Sn. The metal could also be made of other forms of tin, such as $^{115}$Sn, or of other materials that are compatible with the human body environments into which the stents may be placed. Typical materials include metals and alloys such as stainless steel, platinum, shape-memory alloys, such as nitinol, and the like.

The use of $^{117m}$Sn is particularly preferred since it has a half-life of 14 days with an electron energy of 0.13 MeV and 0.15 MeV with no average due to the discrete energy delivery. The depth of conversion electron delivery is thus between 0.22 mm and 0.29 mm which will significantly limit any damage to underlying tissues. In the case of hyperplasia, the majority, if not all the abnormal changes occur in diseased coronary arteries and specifically vulnerable plaque are within a depth of less than 0.33 mm, the conversion electrons emitted by $^{117m}$Sn provide adequate treatment for the abnormal cells while having no adverse effect to the normal cells. Twenty-eight days (two half-lives) is believed to be about the optimum period for neoproliferative tissue suppression and suppression of neointimal proliferation following angioplasty and other primary interventional treatments in the coronary arteries and other vasculature.

The amount of radiation provided by an implant according to the present invention will depend on the purpose of the implant. Implants intended to reduce cell migration and endothelization or to stop all cell activity by destroying cells down to a depth of 0.29 mm from the stent surface will usually have the $^{117m}$Sn plated directly on the surface of the stent to directly contact the wall of the body lumen being treated.

Preferred implants according to the present invention are metal scents with high specific activity $^{117m}$Sn, including $^{117m}$Sn with no carriers added, having a concentration of at least 21 mCi/mg and a total radiation emission in the range from 0.0125 mCi/mm per stent and up to 150 mCi/mm per stent. Stents having lower specific activities are also contemplated where the $^{117m}$Sn may be combined with a carrier and electroplated over the structure of a metal stent.

Stents may be delivered to a target artery or other blood vessel or body lumen in a conventional way. For balloon-expandable stents, they will be delivered over a delivery of balloon and expanded in situ at the target site. For self-expanding stents, they will be delivered while radially constrained, e.g., by an outer sheath, until it is released from constraint in situ at the target luminal site. Such delivery procedures are conventional and well-described in the patent and medical literature.

In one embodiment, substantially the entire scaffold structure of the implant includes an electroplated deposit of $^{117m}$Sn. In another embodiment, the CEES of the implant comprises $^{117m}$Sn as an electroplated deposit upon at least a portion of the scaffold structure. In yet another embodiment, the body member of the implant is made of a metal, comprising $^{115}$Sn, stainless steel, or a shape-memory alloy.

In another embodiment, the CEES of the implant has a non-uniform concentration along the body and provides between 1 and 80 μCi $^{117m}$Sn with higher amounts provided in locations where greater treatment is desired. In another embodiment, one or both ends of the body member of the implant have a higher concentration of CEES than the center.

If desired, the CEES coating can be protected by forming one or more layers of a thin protective film over the CEES coating. The protective film can be formed of any suitable material, including alkene thiol, methyl methacrylate, and noble metals such as gold, silver, platinum, tantalum, and palladium. Preferably, the protective film is transparent with respect to the emitted radiation, such that attenuation of radiation by the protective film layer is negligible. Further, the protective film preferably does not significantly alter the properties of the implant substrate, such as pliability. Furthermore, the protective film is provided at a thickness that is less than the conversion electron emission distance so that the conversion electrons are delivered to the tissue of the lumen. For example, since a tin-117m coated implant emits conversion electrons to an emission distance of about 0.2 to 0.3 mm, the coating thickness must be less than that distance so that the electrons can contact body tissue. If desired, the specific emission distance and coating thickness can be tailored for any particular application to assure even more precise delivery of the radiation to a desired location.

Figure 1:
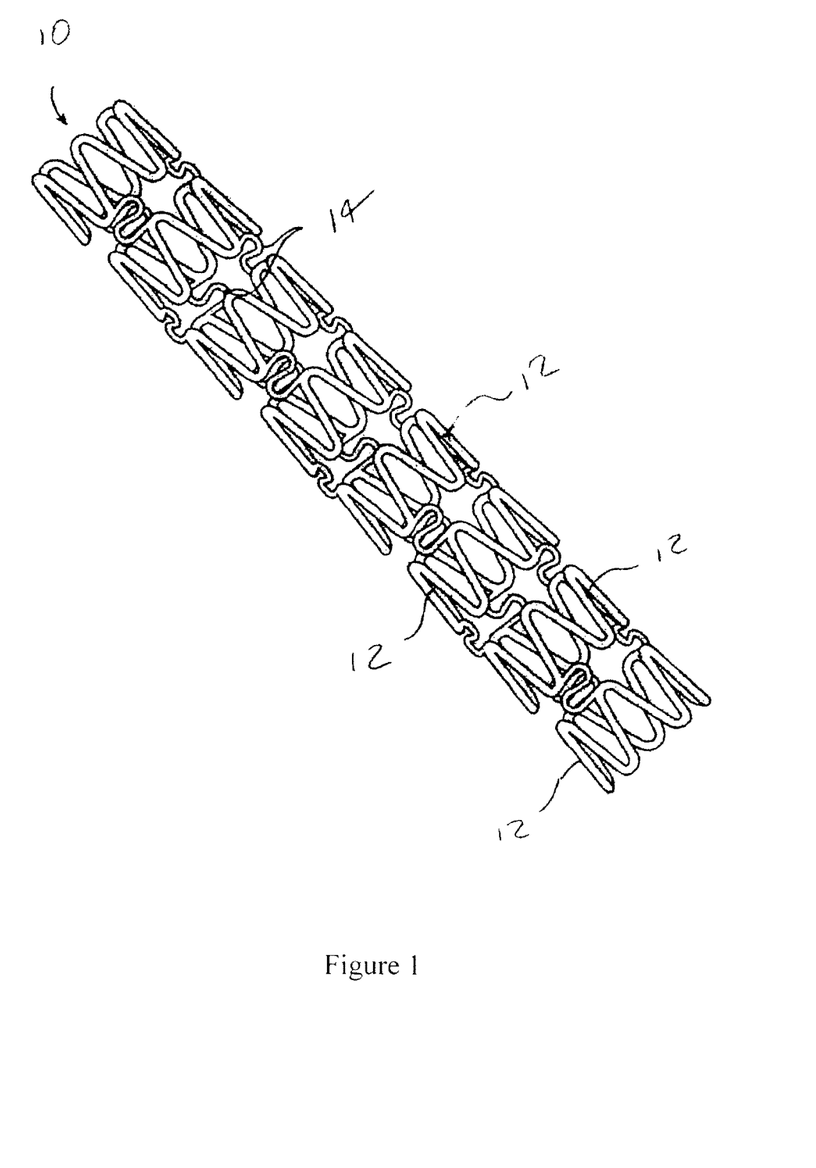
FIG. 1 is a side view of an expandable intraluminal stent according to the invention.

FIG. 1 shows an exemplary implant in the form of a vascular stent 10 is illustrated. The stent 10 comprises a plurality of radially expansible segments 12 joined by serpentine connectors 14. The stent 10 is exemplary and is the common type of coronary stent used for treatment following angioplasty or primary cardiac intervention. The stent will be composed of metal, such as stainless steel, tin, or shape-memory alloy, and will have $^{117m}$Sn incorporated in its structure in any one of the ways described above.

FIGS. 2A-D show profound inhibition of neointima formation by $^{117m}$Sn-electroplated stent implant. Coronary artery implanted with bare metal stent at one month post-implant is seen with moderate concentric fibrocellular neointima (A). When observed under higher magnification, stable healing is observed with relatively high neointimal cell density of modified smooth muscle cells, confluent quiescent endothelium, and relative lack of fibrinoid deposits in neointima (B). In contrast, a stent electroplated with higher-activity $^{117m}$Sn shows profound inhibition of neointima formation (C) as well as mild focal media hemorrhage and neointimal inspissated thrombus, with very attenuated fibrocellular neointimal cap and normal-appearing endothelial cell coverage (D).

Figure 3A:
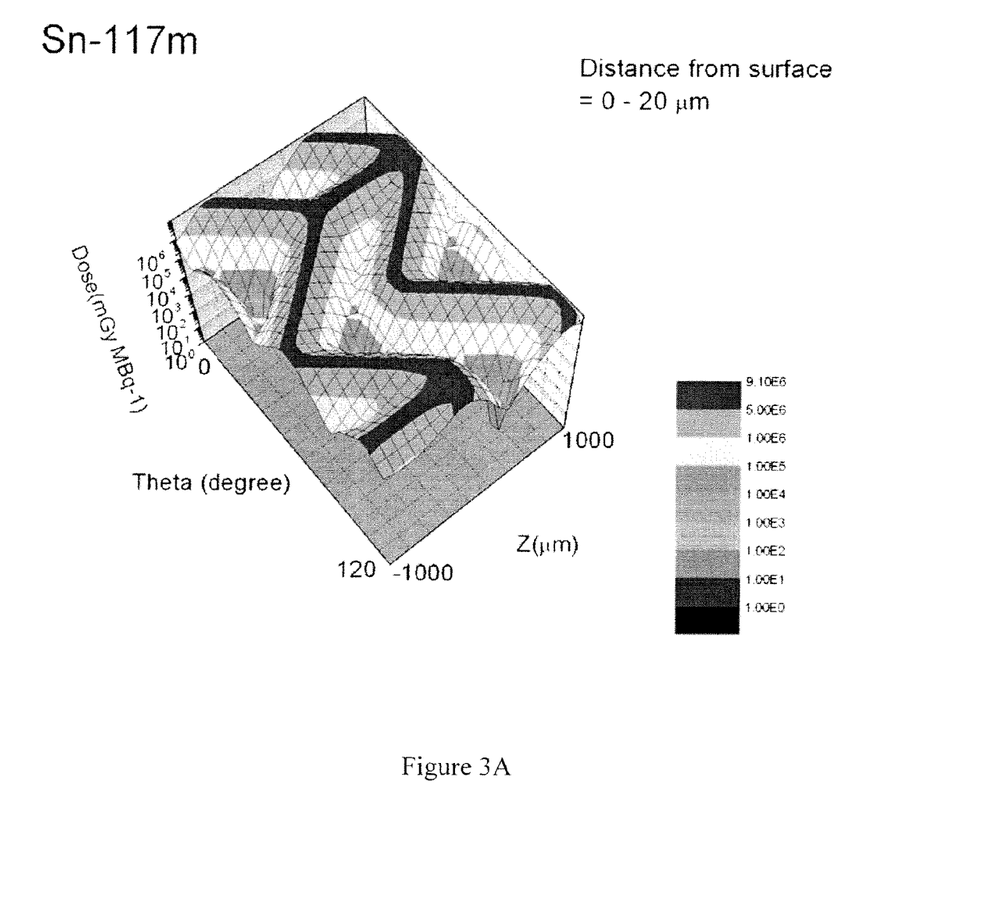
FIGS. 3A-D show the absorbed radiation doses delivered by $^{117m}$Sn (A and B) and $^{32}$P (C and D) in tissue regions 0-20 μm (A, C) and 180-200 μm (B, D) radially into the arterial wall.
Figure 3B:
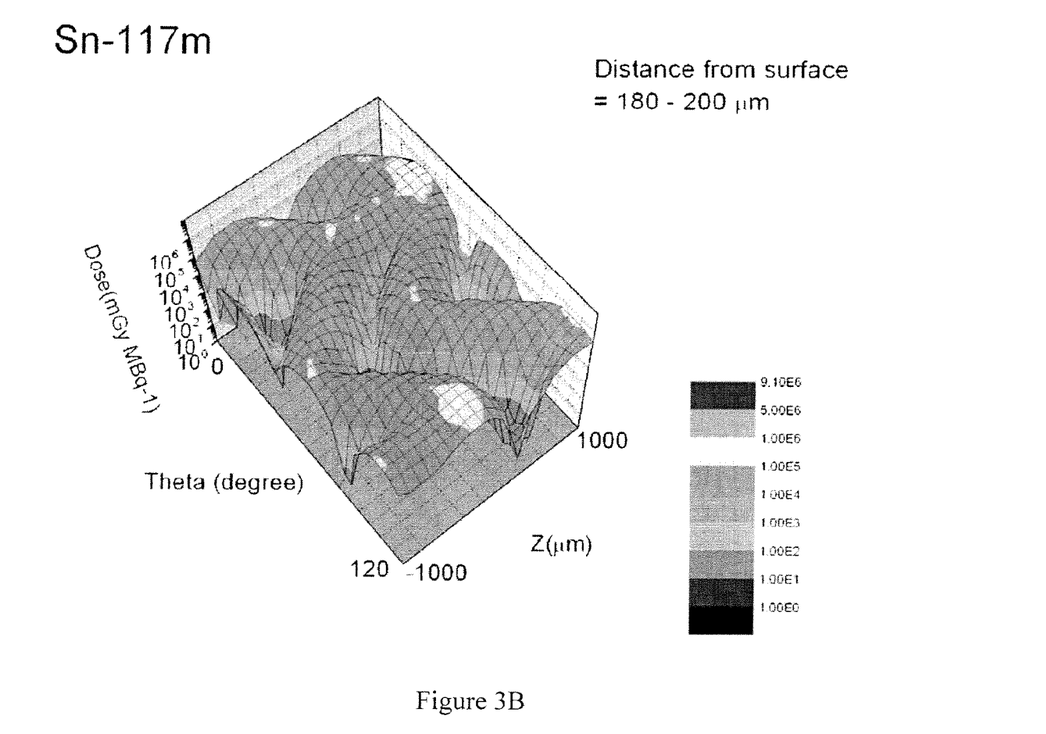
Figure 3C:
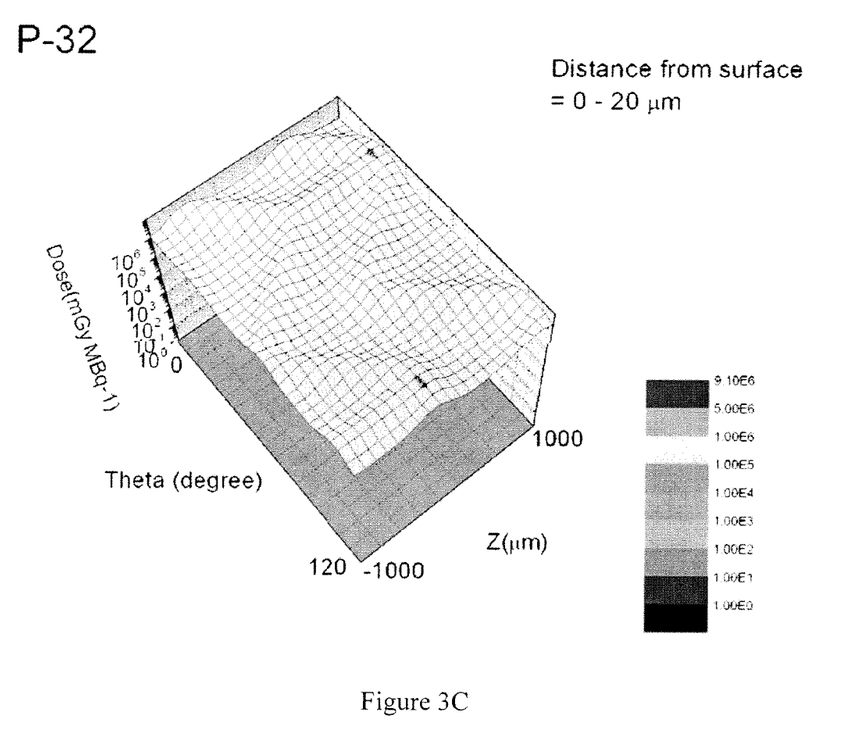
Figure 3D:
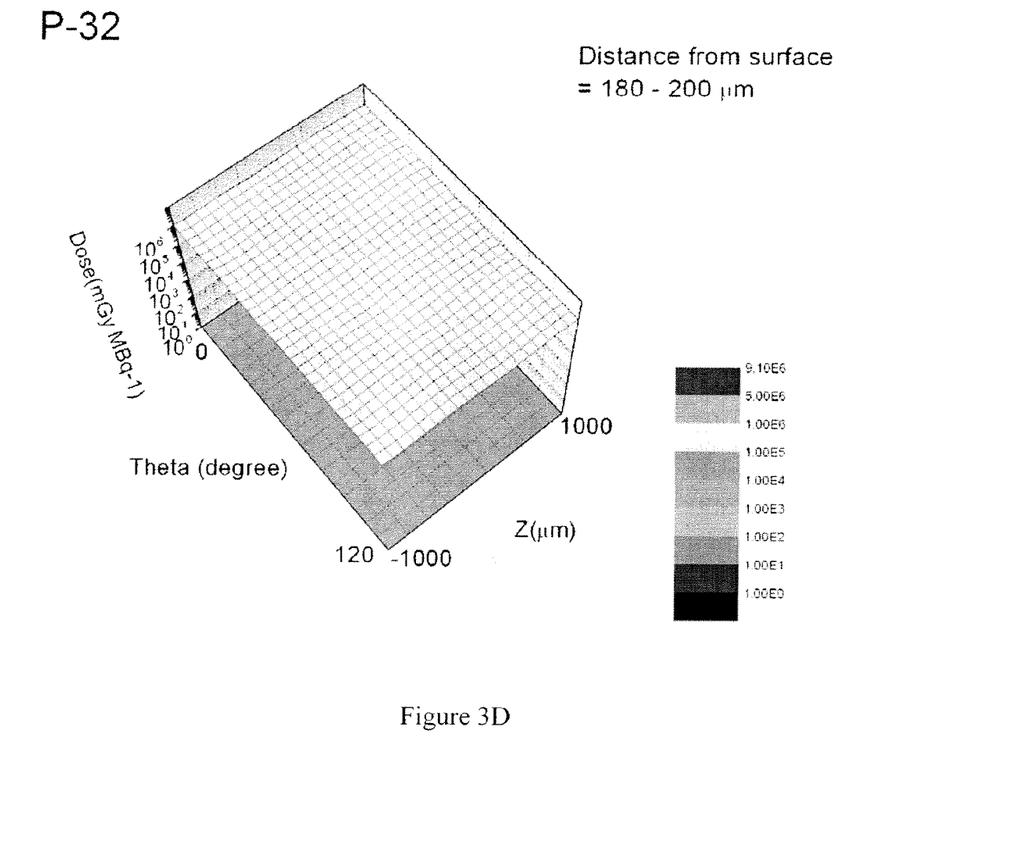

FIGS. 3A-D show the absorbed radiation doses delivered by $^{117m}$Sn and $^{32}$P radially into the arterial wall. FIGS. 3A and 3B show the absorbed radiation doses delivered by $^{117m}$Sn in tissue regions 0-20 μm (A) and 180-200 μm (B) radially into the arterial wall. FIGS. 3C and 3D show the absorbed radiation doses delivered by $^{32}$P in tissue regions 0-20 μm (C) and 180-200 μm (D) radially into the arterial wall.

By comparing absorbed doses delivered by $^{117m}$Sn and $^{32}$P and comparing the tissue regions from 0-20 microns and from 180-200 microns and all tissue depth in between, a comparison of effective dosimetry has been made between the two isotopes with predictions of efficacy. The dosimetry calculations in the present invention allow the calculation of the optimal amount of $^{117m}$Sn to be electroplated onto a coronary artery stent as well as for the prediction and appropriate therapy of vascular and other lumen that are diseased. The dosimetry calculations make it possible to create absorbed doses to critical targets in the arterial wall.

EXAMPLES

The following examples illustrate preferred device configurations and their use.

Example 1

Electroplating of ACS MultiLink™ Stent

ACS MultiLink™ stents are first thoroughly rinsed by acetone or ethyl alcohol (with sonication if needed) to remove adventitious grease and dust particles. A pair of tweezers is inserted into the stent prior to electroplating so that $^{117m}$Sn activity is restricted to the outside surfaces of the wire to prevent substantial irradiation of the lumen.

Then the stents are submerged in the activation and plating solution comprising either 0.5M $CoCl_2$ and 1M HCl or 0.1-0.2M $NiCl_2$ and 2M HCl, at a current density of 5-10 mA/cm$^2$, for about 1-3 min. Hydrochloric acid activates stents by dissolving the passive film on stainless steel and the metal ion $Co^{2+}$ or $Ni^{2+}$ nucleates on steel to generate a "seed" layer and provide better bonding of Sn to steel. Cobalt or nickel deposition is followed by a quick rinsing with water and transferring to a Sn plating solution, to which the potential is quickly applied to avoid significant dissolution of Co or Ni. The Sn plating solution comprises either $(1-8) \times 10^{-3}$M $Sn^{2+}$, 0.2 M $H_2SO_4$, 0.1 M HCl and 2 g/l of resorcinol or $1 \times 10^{-2}$M $Sn^{2+}$, 2M HCl, 0.2 M $H_2SO_4$ and 2 g/l of gelatin. The electroplating is carried out at room temperature with either potentiostatic or galvanostatic deposition at the potential E=−0.5 to −0.55V vs. Ag/AgCl/Cl$^-$ reference electrode and the current density is 0.1-0.5 mA/cm$^2$. In addition, $10^{-7}$-$10^{-2}$M Tl is added to the plating solution to reduce the rate of H$_2$ evolution, which decreases the quality of Sn coating.

To prepare the plating solution from the radioactive stannic tin, a weighed piece of high purity tin wire is placed in a dissolution vessel along with an aliquot of radioactive tin and 12M hydrochloric acid to establish an equilibrium such that the radioactive tin behaves like the "bold" tin (both as Sn$^{2+}$).

The quality of the Sn coating is checked by standard tests for bonding and adhesion using scotch tape and bending the wire constituting the stent at 90 degrees. If the deposit does not peel off with the tape, or no cracks occur upon bending, the adhesion can be considered satisfactory.

Example 2

Dosimetry Calculations for Recommended Loading of $^{117m}$Sn Radioactivity for Electroplating of ACS MultiLink™ Stents To determine the optimal amount of $^{117m}$Sn to electroplate onto the ACS MultiLink™ stent, it is assumed that equal absorbed doses delivered by $^{117m}$Sn and $^{32}$P will cause the same biological response. This assumption is reasonable considering that it is generally accepted that the 125-160 keV conversion electrons emitted by $^{117m}$Sn (principal source of absorbed dose) are radiobiologically similar to the energetic beta particles emitted by $^{32}$P. Furthermore, the similar physical half-lives of the two radionuclides will result in similar exponentially decreasing dose rate patterns.

The absorbed doses delivered by $^{117m}$Sn and $^{32}$P in tissue regions 0-20 µm and 180-200 µm radially into the arterial wall have been plotted as shown in FIGS. 3A-D. Table 1 summarizes the relevant maximum absorbed doses, and the ratios of the corresponding values for $^{32}$P and $^{117m}$Sn. When the tissue region from 0-20 µm is the critical target, to match the maximum dose achieved by the $^{32}$P stent, the $^{117m}$Sn stent should be coated with about one-half of the optimal activity for $^{32}$P. When the tissue region from 180-200 µm is taken as the critical target, then the $^{117m}$Sn stent should be coated with about 2.5 times the optimal activity for $^{32}$P. These calculations apply to the ACS MultiLine™ stent expanded at 8 atm to a diameter of 2.5 mm and only the outer half of the wire surfaces of the stent are coated with the radionuclide. When $^{117m}$Sn activity is coated across the total wire surfaces, the amount of $^{117m}$Sn activity electroplated onto the stent should be increased by a factor of approximately two.

TABLE 1

Maximum Absorbed Doses to Critical Targets in the Arterial Wall per MBq of Activity Distributed Over the Outer One-Half of the Wire Surfaces of the ACS MultiLink ™ Stent

| | Radial distance of 0-20 µm | Radial distance of 180-200 µm |
|---|---|---|
| $^{32}$P | 5.0 × 10$^6$ mGy | 1.4 × 10$^6$ mGy |
| $^{117m}$Sn | 9.1 × 10$^6$ mGy | 5.8 × 10$^5$ mGy |
| Ratio ($^{32}$P/$^{117m}$Sn) | 0.55 | 2.4 |

Example 3

Treatment of Bone Pain with $^{117m}$Sn DTPA $^{117m}$Sn is produced by neutron bombardment of enriched Sn-117 and chelated to diethylenetriaminepentaacetic acid to form $^{117m}$Sn DTPA. Specific activity of $^{117m}$Sn ranges from 3 to 15 mCi/mg at end of bombardment. $^{117m}$Sn decays by isometric transition with the emission of monoenergetic conversion electrons (127, 129, 152 and 155 keV with a combined abundance of 110%), as summarized in Table 2.

TABLE 2

$^{117m}$Sn Decay Data ($t_{1/2}$ = 14 days)

| Major Radiations | Energy (keV) | Intensity (%) |
|---|---|---|
| Auger-L | 3 | 91.0 |
| Auger-K | 21 | 10.8 |
| CE-K1 | 126.8 | 64.8 |
| CE-K2 | 129.4 | 11.7 |
| CE-L1 | 151.6 | 26.1 |
| CE-L2 | 154.1 | 1.5 |
| CE-M1 | 155.1 | 5.6 |
| Gamma | 158.6 | 86.4 |

For treatment of bone pain with $^{117m}$Sn DTPA, the physical characteristics of $^{117m}$Sn have been measured and compared with other radionuclides useful for similar therapies. As shown in Table 3, $^{117m}$Sn has dominantly (86%) Gamma photons and the shortest average range. Because of their limited and discrete range (0.22 mm and 0.29 mm) in tissue, the electrons emitted from the decay of $^{117m}$Sn permit large bone radiation doses without excessive radiation to the bone marrow. Furthermore, the physical half-life of 14 days provides an intermediate dose rate and allows adequate shelf-life of the radiopharmaceutical.

TABLE 3

Physical Characteristics of Radionuclides useful for Bone Pain Therapy[a]

| Nuclide | Maximum $E_\beta$ (MeV) | Weighted Avg. $E_\beta$ (MeV) | Avg. Range[b] (mm) | Half-Life (days) | Gamma Photons (MeV) |
|---|---|---|---|---|---|
| Sr-89 | 1.46 | 0.583 | 2.4 | 50.5 | None |
| Re-186 | 1.08 | 0.349 | 1.05 | 3.71 | 0.137 (9.2%) |
| Sm-153 | 0.81 | 0.234 | 0.55 | 1.93 | 0.103 (28%) |
| P-32 | 1.71 | 0.695 | 3.0 | 14.3 | None |
| Sn-117m | 0.127[c] | — | 0.21[d] | 14.0 | 0.159 (86%) |
| | 0.152[c] | — | 0.29[d] | | |

[a]MIRD: Radionuclide Data and Decay Schemes. Society of Nuclear Medicine, 1989.
[b]In water, Health Physics and Radiological Handbook, Nuclear Lectern Associates, 1984.
[c]Monoenergetic conversion electron, not beta particle.
[d]Discrete travel of emitted conversion electron (not an average).

The radionuclidic purity of the $^{117m}$Sn will be ≥85% throughout the shelf life of the product. Decay properties of the possible radionuclide impurities and maximum levels at calibration and expiration are listed in Table 4. Radiochemical purity is determined post-manufacture using high-performance liquid chromatography (HPLC) and instant thin-layer chromatography (ITLC). Radiochemical purity of $^{117m}$Sn DTPA is ≥90%. Possible impurities are the stannous form of the $^{117m}$Sn DTPA chelate (≤5.0%) and $^{117m}$Sn non-mobiles (≤5.0%).

TABLE 4

Decay Properties and Levels of Potential Radionuclidic Impurities

| Nuclide | Calibr. % | Expir. % | Half-Life | Decay Mode | Energy (MeV) |
|---|---|---|---|---|---|
| Sn-117m | ≥93.0 | ≥85.47 | 14.0 d | IT, γ | 0.159 |
| Sn-113 | ≤3.4 | ≤8.49 | 115 d | γ | 0.255 |

TABLE 4-continued

Decay Properties and Levels of Potential Radionuclidic Impurities

| Nuclide | Calibr. % | Expir. % | Half-Life | Decay Mode | Energy (MeV) |
|---|---|---|---|---|---|
| Sn-125 | ≤1.6 | ≤0.88 | 9.65 d | β⁻ avg | 0.813 |
|  |  |  |  | β⁻ max | 2.36 |
| Sb-124 | ≤0.2 | ≤0.44 | 60.2 d | β⁻ avg | 0.378 |
|  |  |  |  | β⁻ max | 2.30 |
| Sb-125 | ≤0.8 | ≤2.26 | 2.73 y | β⁻ avg | 0.086 |
|  |  |  |  | β⁻ max | 0.622 |
| Sb-126 | ≤0.2 | ≤0.16 | 12.4 d | β⁻ avg | 0.289 |
|  |  |  |  | β⁻ max | 1.79 |
| Other* | ≤0.8 | ≤2.30 |  |  |  |

*Co-60, Ag-110, Zn-65

The formulation of the final drug product is summarized in Table 5. Each vial will contain 13.8±1.1mCi of $^{117m}$Sn at a concentration of 8.3 mCi/mL at time of calibration. The pH of the final solution is between 3.0 and 5.0. the drug product is formulated in Water-for-Injection and may also contain sodium chloride from pH adjustment. The vial contents are sterile and nonpyrogenic.

TABLE 5

Components of stannic Pentetate $^{117m}$Sn injection at calibration

| Component | Quantity per mL |
|---|---|
| Sn | ≤3.5 mg/mL |
| DTPA | ≤280 mg/mL* |
| CaCl$_2$•2H$_2$O | ≤23.1 mg/mL* |
| H$_2$O$_2$ | ≤2.45 mg/mL |

*The ratio of Sn:DTPA:CaCl$_2$•2H$_2$O will be fixed at 1.0 mg:67 mg:20 mg.

Example 4

Prevention of Hyperplasia with $^{117m}$Sn Electroplated Stents

Nine stents were implanted in the coronary arteries of three juvenile castrated male farm pigs (33-36 kg) by standard procedures: bare metal stent (n=1 vessel); non-radioactive Sn stents (n=2 vessels, 200-400 µg non-radioactive Sn); stents electroplated with 30 uCi $^{117m}$Sn (n=3 vessels) and stents electroplated with 80 uCi $^{117m}$Sn (n=3 vessels). Four weeks later, these pigs underwent angiographic restudy and the hearts were perfusion fixed. Standard methods were used to prepare and evaluate histologic sections of the stented coronary arteries with standard procedures.

Figure 2:
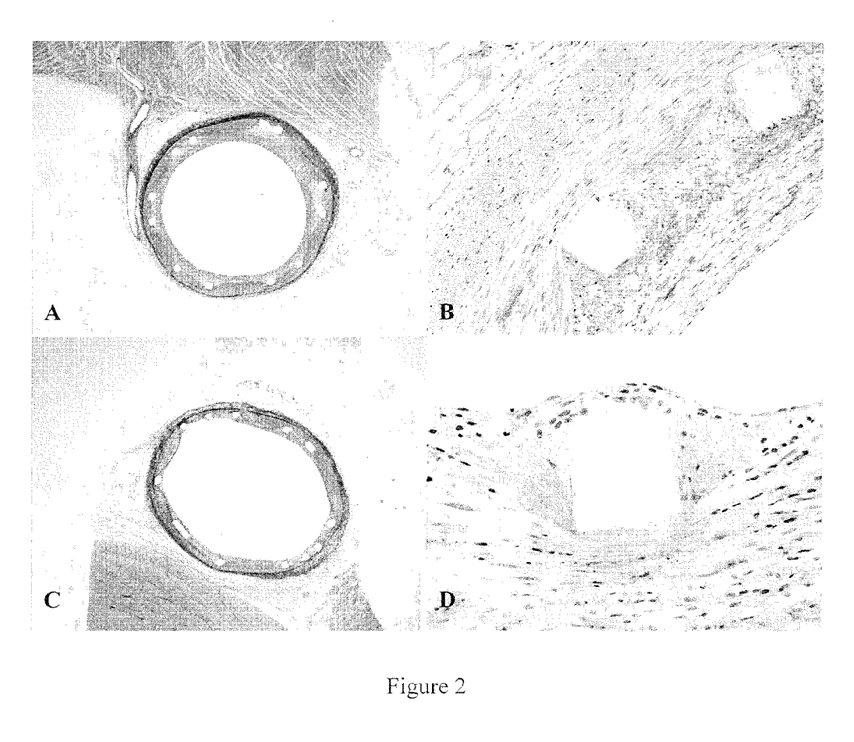
FIGS. 2A-D show profound inhibition of neointima formation by $^{117m}$Sn-electroplated stent implant. Coronary artery implanted with bare metal stent (A and B) and $^{117m}$Sn-electroplated stent (C and D) at one month post-implantation.

Exemplary results are shown in FIGS. 2A-D. FIGS. 2A-B show a coronary artery implanted with a bare metal stent. At low magnification (A), moderate concentric fibrocellular neointima is readily observed. At higher magnification (B), tunica media can be seen compressed with only very minimal, focal smooth muscle cell necrosis. In addition, stable healing is seen with relatively high neointimal cell density of modified smooth muscle cells, confluent quiescent endothelium, and relative lack of fibrinoid deposits in neointima. In contrast, FIGS. 2C-2D show a stent electroplated with 80 uCi $^{17m}$Sn with no obvious neointima formation. At higher magnification (D), mild focal media hemorrhage and neointimal inspissated thrombus was observed, with very attenuated fibrocellular neointimal cap and normal-appearing endothelial cell coverage.

Example 5

Dosimetry Calculations for Different Batches of $^{117m}$Sn Electroplated Stents The half-life ($t_{1/2}$) of $^{117m}$Sn is 14 days and the effective therapeutic time is 28 days (two half-lives). The storage time can be increased by either increasing the purity of the $^{117m}$Sn per mg or by increasing the amount of the $^{117m}$Sn electroplated to the stent to allow for the radioactive decay. Monthly preparation and distribution of stent batches to cardiovascular user-centers, such as hospitals or local distribution centers, can be carried out as follows. Each stent batch would have a 3 to 5 day window-of-use differential (quantitatively) of plated stents and this will accomplish adequate availability of stents for use so that shipping of stents can be performed on a monthly basis. For example, if a first stent batch has a 5 day usability window from the time of delivery to the cardiovascular user-center until the time the stent must be put into a human coronary artery, this stent would have a set mCi/mm and mCi/mg level of radioactivity placed on it for calendar days 1 through 5, e.g. usability days March 1 through 5.

For a second stent batch delivered on the first day of March but for use on days 6 though 10 of the month, the radioactivity level of plating or deposition would be that of first stent batch plus the average decay for 5 days so that on day 6 of March, the stent would have the same radioactivity as the first stent batch on March 1. On March 1 a set of stents for use on March 10 through March 15 would also be delivered but would have plating of $^{117m}$Sn radioactivity levels as that of the first stent batch plus enough $^{117m}$Sn to compensate for 10 days of decay so that the third stent batch would have the same radioactivity on day 10 of March as the first stent batch has on day 1 of March. The fourth through sixth stent batches would have proportionally larger amounts of $^{117m}$Sn deposited on them to equal the radioactivity as the first stent batch for use on its first designated and approved day. In this example a total of six batches of stents could be delivered on the first part of each month with each batch implantable for successive five day intervals during the month.

While the above is a description of the preferred embodiments of the invention, various alternatives, modifications, and equivalents may be used. Therefore, the above description should not be taken as limiting the scope of the invention which is defined by the claims.

What is claimed is:

1. An implant comprising a body member and a conversion electron emitting source (CEES) associated with selected locations of the body member, with the CEES providing conversion electrons that are emitted to provide radiation dosimetry immediately adjacent the selected locations while not affecting surrounding tissue outside of the immediately adjacent area, and wherein the implant is hollow having interior and exterior surfaces, with the CEES provided only on the exterior surface so that the conversion electrons are not provided in the interior surface of the implant; and
    wherein said CEES is Sn$^{117m}$ at a dose of 0.0125 to 150 mCi/mm.

2. The implant of claim 1, wherein the body member is configured and dimensioned to conform to organs or fluid vessels associated therewith with the selected locations of CEES provided at least where the body member contacts the organs or fluid vessels.

3. The implant of claim 2 wherein the CEES is provided on selected locations of the body member in the form of an adherent selective coating.

4. The implant of claim 1, wherein the body member includes an expandable scaffold structure so that it can assume a first placement configuration and a second treatment configuration wherein the conversion electrons are emitted by a distance of 0.2-0.3 mm into adjacent tissue.

5. The implant of claim 4, wherein the CEES comprises $^{117m}$Sn as an electroplated deposit upon at least a portion of the scaffold structure.

6. The implant of claim 5, wherein substantially the entire exterior surface of the scaffold structure includes an electroplated deposit of $^{117m}$Sn.

7. The implant of claim 1, wherein the body member is made of a metal that is compatible with the intended environment.

8. The implant of claim 7, wherein the metal comprises $^{115}$Sn, stainless steel, or a shape-memory alloy.

9. The implant of claim 1, wherein the CEES has a higher concentration at least one end of the body member.

10. The implant of claim 9, wherein each end of the body member has a higher concentration of CEES than the center.

11. The implant of claim 9, wherein the CEES has a lower concentration at each end of the body member than in the center.

12. The implant of claim 1, wherein the implant is a vascular stent.

13. The implant of claim 1 wherein the exterior surface of the implant includes a coating having a thickness less than an emission distance of said CEES.

14. The implant of claim 1 wherein the exterior surface of the implant includes a coating having a thickness less than about 0.2 to 0.3 mm.

15. The implant of claim 1 wherein said $Sn^{117m}$ is no-carrier added tin 117m.

16. A method of selectively providing radiation dosimetry to a subject in need of same, which comprises placing the implant of claim 1 adjacent, upon or within an organ or fluid vessel associated with the organ in a manner such that the selected locations of the implant containing the CEES are provided at least were the body member contacts the organ or fluid vessel to provide conversion electrons thereto for such treatment.

17. The method of claim 16 which comprises providing a CEES source that provides hyperplasia inhibiting radiation for treatment of hyperplasia in the subject.

\* \* \* \* \*